United States Patent
Newham (10) Patent No.: US 9,603,956 B2
(45) Date of Patent: Mar. 28, 2017

(54) DYNAMIC ENHANCED AND DIFFUSE BROAD SPECTRUM UVC OR ALTERNATIVE CONTROLLED IONIZING RADIATION SOURCE EMITTERS FOR MOBILE AND FIXED PLACEMENT DISINFECTION OF CLINICAL SURFACES

(71) Applicant: Paul Newham, San Antonio, TX (US)

(72) Inventor: Paul Newham, San Antonio, TX (US)

( * ) Notice: Subject to any disclaimer, the term of this patent is extended or adjusted under 35 U.S.C. 154(b) by 0 days.

(21) Appl. No.: 14/569,008

(22) Filed: Dec. 12, 2014

(65) Prior Publication Data

US 2015/0196674 A1    Jul. 16, 2015

Related U.S. Application Data

(60) Provisional application No. 61/915,450, filed on Dec. 12, 2013.

(51) Int. Cl.
| | | |
|---|---|---|
| *H01J 37/00* | (2006.01) | |
| *A61L 2/10* | (2006.01) | |
| *F21V 14/04* | (2006.01) | |
| *F21V 5/04* | (2006.01) | |
| *F21V 13/06* | (2006.01) | |
| *G02B 5/02* | (2006.01) | |
| *A61L 2/24* | (2006.01) | |

(52) U.S. Cl.
CPC ............... *A61L 2/10* (2013.01); *F21V 5/045* (2013.01); *F21V 13/06* (2013.01); *F21V 14/04* (2013.01); *G02B 5/0231* (2013.01); *G02B 5/0284* (2013.01); *A61L 2/24* (2013.01)

(58) Field of Classification Search
None
See application file for complete search history.

(56) References Cited

U.S. PATENT DOCUMENTS

| | | | | |
|---|---|---|---|---|
| 6,254,625 B1 * | 7/2001 | Rosenthal | ................. | A61L 2/10 606/10 |
| 7,888,656 B2 * | 2/2011 | Freedgood | ................ | A61L 2/10 250/453.11 |
| 8,029,739 B2 * | 10/2011 | Field | ..................... | A47L 11/283 422/22 |
| 8,277,724 B2 * | 10/2012 | Jung | ......................... | A61L 2/10 422/1 |
| 8,481,970 B2 * | 7/2013 | Cooper | ..................... | A61L 2/10 250/453.11 |

(Continued)

FOREIGN PATENT DOCUMENTS

| | | | |
|---|---|---|---|
| CN | 102210882 A | * | 10/2011 |
| CN | 203610006 U | * | 5/2014 |
| CN | 102210882 B | * | 8/2014 |

*Primary Examiner* — Andrew Smyth
(74) *Attorney, Agent, or Firm* — Kammer Browning PLLC (57) ABSTRACT

A system providing effective, broad spectrum UV-C or other ionizing radiation clinical surface disinfection, high intensity UV-C light emitting diodes (LEDs) of incrementally differing wavelengths are sequentially embedded in densely packed reflective nacels (cups or pockets) forming the surface of a rotating spherical or hemispherical structure. A combination of UV-C emitter component location and activation with the rotational and reciprocal elevation functions of such structures produces complete and continuous environmental overlapping UV-C energy scattering.

14 Claims, 6 Drawing Sheets

(56) References Cited

U.S. PATENT DOCUMENTS

| | | | | | |
|---|---|---|---|---|---|
| 8,506,195 B2* | 8/2013 | Diaz | | A46B 11/002 | 250/455.11 |
| 8,569,715 B1* | 10/2013 | Tantillo | | A61L 2/10 | 250/453.11 |
| 8,575,567 B2* | 11/2013 | Lyslo | | A61L 2/10 | 250/455.11 |
| 8,791,441 B1* | 7/2014 | Lichtblau | | A61L 2/10 | 250/455.11 |
| 9,023,274 B2* | 5/2015 | Garner | | A61L 2/10 | 250/454.11 |
| 2006/0216193 A1* | 9/2006 | Johnson | | A61L 2/10 | 422/24 |
| 2007/0207066 A1* | 9/2007 | Thur | | A61L 9/205 | 422/121 |
| 2007/0209144 A1* | 9/2007 | Fester | | A47L 5/30 | 15/339 |
| 2007/0276455 A1* | 11/2007 | Fiset | | A61C 19/066 | 607/91 |
| 2010/0181582 A1* | 7/2010 | Li | | H01L 33/44 | 257/91 |
| 2010/0187443 A1* | 7/2010 | Leben | | A61L 2/10 | 250/492.1 |
| 2011/0113574 A1* | 5/2011 | Fulmer | | A46B 9/02 | 15/21.1 |
| 2011/0243789 A1* | 10/2011 | Roberts | | A61L 2/10 | 422/24 |
| 2012/0093688 A1* | 4/2012 | Harmon | | A61L 2/10 | 422/24 |
| 2012/0126134 A1* | 5/2012 | Deal | | A61L 2/10 | 250/372 |
| 2012/0223216 A1* | 9/2012 | Flaherty | | A61L 2/10 | 250/214.1 |
| 2012/0273340 A1* | 11/2012 | Felix | | B01D 53/007 | 204/157.3 |
| 2012/0305787 A1* | 12/2012 | Henson | | A61L 2/10 | 250/372 |
| 2013/0047357 A1* | 2/2013 | Diaz | | A46B 11/002 | 15/104.94 |
| 2014/0084185 A1* | 3/2014 | Palmer | | A61L 9/20 | 250/504 R |
| 2014/0158917 A1* | 6/2014 | Stibich | | A61L 2/10 | 250/504 R |
| 2014/0161663 A1* | 6/2014 | Farren | | A61L 2/10 | 422/24 |
| 2014/0175280 A1* | 6/2014 | Tantillo | | A63H 33/006 | 250/338.1 |
| 2014/0329227 A1* | 11/2014 | Ssultz | | A61L 2/10 | 435/5 |

* cited by examiner

DYNAMIC ENHANCED AND DIFFUSE BROAD SPECTRUM UVC OR ALTERNATIVE CONTROLLED IONIZING RADIATION SOURCE EMITTERS FOR MOBILE AND FIXED PLACEMENT DISINFECTION OF CLINICAL SURFACES

CROSS REFERENCES TO RELATED APPLICATIONS

This application claims the benefit under Title 35 United States Code §119(e) of U.S. Provisional Patent Application Ser. No. 61/915,450 filed Dec. 12, 2013, the full disclosure of which is incorporated herein by reference.

BACKGROUND OF THE INVENTION

1. Field of the Invention

To provide effective, broad spectrum UV-C or alternative controlled ionizing radiation source clinical surface disinfection, high intensity light emitting diodes (LEDs) of incrementally differing wavelengths are sequentially embedded in densely packed reflective nacels (geometrically shaped cups or depressions) forming the surface of a rotating spherical or hemispherical structure. The combination of emitter component location and activation with the rotational and reciprocal elevation functions of such structures produces complete and continuous environmental overlapping energy scattering. Ultraviolet C light (UV-C or UVC) is an ISO Standard for short wave UV light in the 280-100 nm range with energy per photon in the 4.43-12.4 eV range. Alternate ionizing radiation sources include controlled x-ray and gamma emissions.

2. Description of the Related Art

The present invention relates in general to Hospital Acquired Infections (HAI) and the no-touch disinfection of high-touch clinical environment surfaces, which when used in combination with conventional chemical cleaning techniques have been shown effective in increasing patient safety. Commonly used no-touch methods most often in use include the use of hydrogen peroxide vapor or UV-C ultraviolet light irradiation which forms the basis for this invention.

While gaining awareness in the healthcare environment, present UV-C emission devices suffer the inherent problems of: (a) Fundamental design limitations resulting in difficult aiming of the device energy field with respect to critical high-touch patient surfaces which can end up being shadowed in blind spot locations, greatly compromising effective disinfection. Attempts to rectify this problem with reflective room coatings or frequent system repositioning during use are costly and/or disruptive; (b) limited UV-C spectrum emission through the use of mercury discharge or xenon emitters thereby compromising effective disinfection of the wide assortment of prospective HAI pathogens (including MRSA, *C. difficile, Acinetobacter, A. baumanni*, Vancomycin resistant enterobacter VRE, etc.). While many current UV-C systems exhibit a limited wavelength spectrum of around 253 nm, optimal UV-C disinfection effectiveness occurs through broad as possible use of a 200-280 nm emission spectrum; (c) present systems are heavy, bulky semi-transportable devices presenting significant operator problems in transportation, set-up and operation. They may also lack on-board power and adequate, automated security of operation. They are also relatively costly, thereby limiting their use.

The present invention relates in general to Hospital Acquired Infections (HAI) and the no-touch disinfection of high-touch clinical environment surfaces, which when used in combination with conventional chemical cleaning techniques have been shown effective in increasing patient safety. Commonly used no-touch methods most often in use include the use of hydrogen peroxide vapor or UV-C ultraviolet light irradiation which forms the basis for this invention.

While gaining awareness in the healthcare environment, present UV-C emission devices suffer the inherent problems of: (a) Fundamental design limitations resulting in difficult aiming of the device energy field with respect to critical high-touch patient surfaces which can end up being shadowed in blind spot locations, greatly compromising effective disinfection. Attempts to rectify this problem with reflective room coatings or frequent system repositioning during use are costly and/or disruptive; (b) limited UV-C spectrum emission through the use of mercury discharge or xenon emitters thereby compromising effective disinfection of the wide assortment of prospective HAI pathogens (including MRSA, *C. difficile, Acinetobacter, A. baumanni*, Vancomycin resistant enterobacter VRE, etc.). While many current UV-C systems exhibit a limited wavelength spectrum of around 253 nm, optimal UV-C disinfection effectiveness occurs through broad as possible use of a 200-280 nm emission spectrum; (c) present systems are heavy, bulky semi-transportable devices presenting significant operator problems in transportation, set-up and operation. They may also lack on-board power and adequate, automated security of operation. They are also relatively costly, thereby limiting their use.

SUMMARY OF THE INVENTION

According to the present invention, the device consists of high intensity UV-C light emitting diodes (LEDs) or alternative UV-C emission components of incrementally differing wavelengths which, in association with white light LEDs, are sequentially embedded in densely packed reflective nacels which form the surface of a rotatable spherical or hemispherical structure. Each group of a central nacel and its immediate surrounding partners (a group of 6 in the case of hexagonal nacels) forms a pod, emitting a broad spectrum UV-C energy output. By incrementally re-sequencing each UV-C LED emitter in adjacent pods while rotating and strobing the entire spherical or hemispherical support structure, extreme broad spectrum UV-C energy is evenly diffused over the treatment area. This energy diffusion is further enhanced through continuous reciprocal raising and lowering of the rotating spherical and hemispherical UV-C emitter head structure of the free-standing, mobile embodiment and ceiling or wall mount embodiment of the device during use.

The invention also shows the incorporation of white light LEDs within each reflective nacel, providing the system operator with the initial ability to correctly aim/position the UV-C emitter head relative to treatment surfaces prior to UV-C energy activation.

The invention also shows incorporation of automatic UV-C dosage completion monitoring of treated surfaces, results of which are wirelessly communicated within the system enabling auto-shutdown at service completion.

The invention also shows multi directional, embedded external motion detection sensing providing automatic system shutdown during use should inadvertent human presence be detected in the treatment area.

The invention also shows operator controls to incorporate effective system activation security through the use of microchip embedded operator card readers and associated passcode input keypads.

The invention also shows that each system control unit is individually digitally encoded to its specific system unit (when not hard wired) thereby preventing system cross-talk.

The invention also shows that UV-C energy system activation is time delayed (30 seconds, for example) following operator switch-on, enabling operator departure from the treatment area.

The invention also shows each system to have a prominent emergency switch-off control.

The invention also shows that in the embodiment with a permanent ceiling or wall mounted hemispherical system UV-C emitter, the operator control unit communicates wirelessly with such a unit and displays internal battery condition, if so powered.

The invention also shows that the free-standing mobile embodiment of the device incorporates rechargeable battery power supplies in addition to being AC line powered as desired.

DETAILED DESCRIPTION OF THE PREFERRED EMBODIMENT

Figure 1:
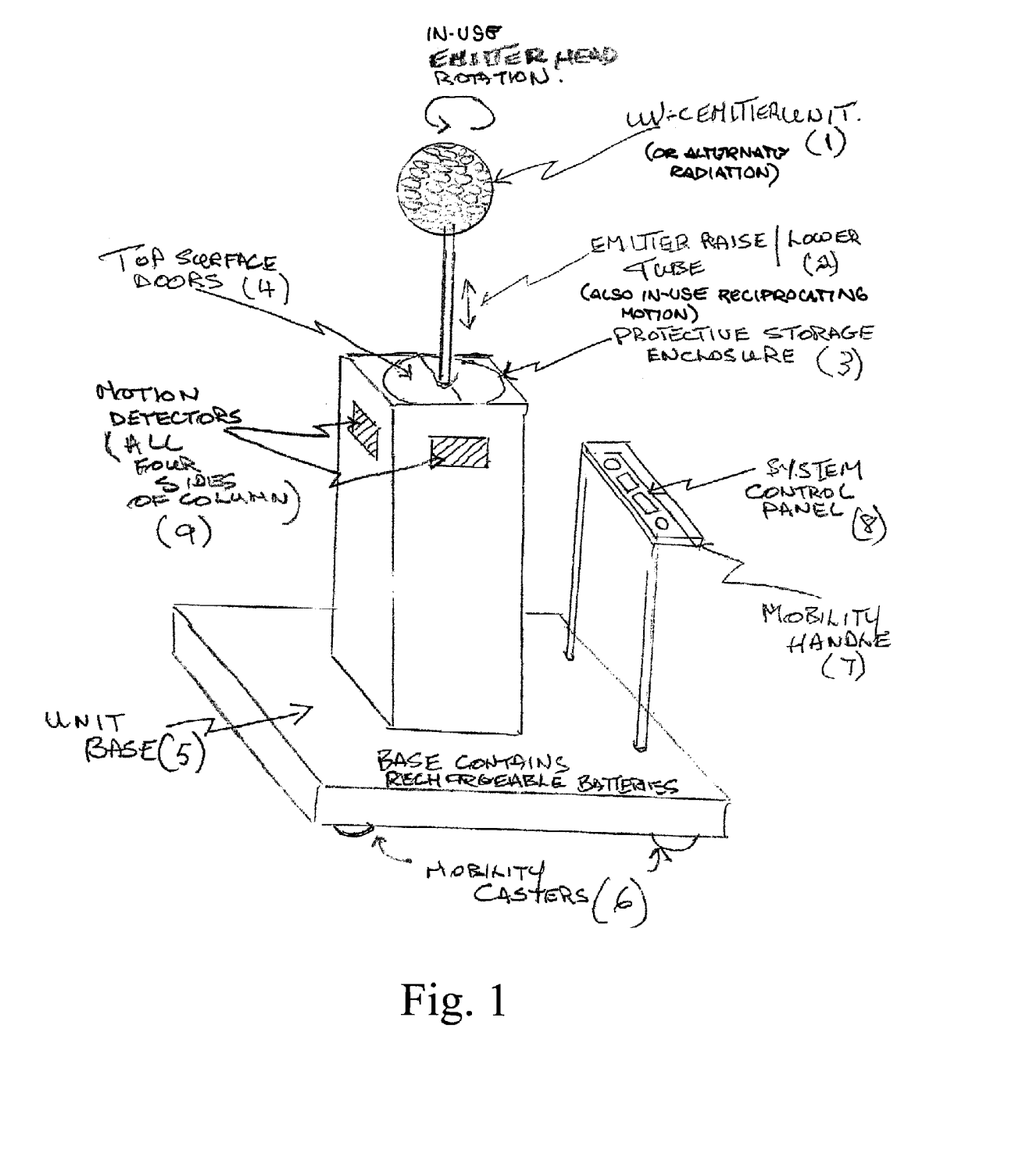
FIG. 1 shows a view of a free-standing, mobile embodiment of the device of the present invention.
Figure 2:
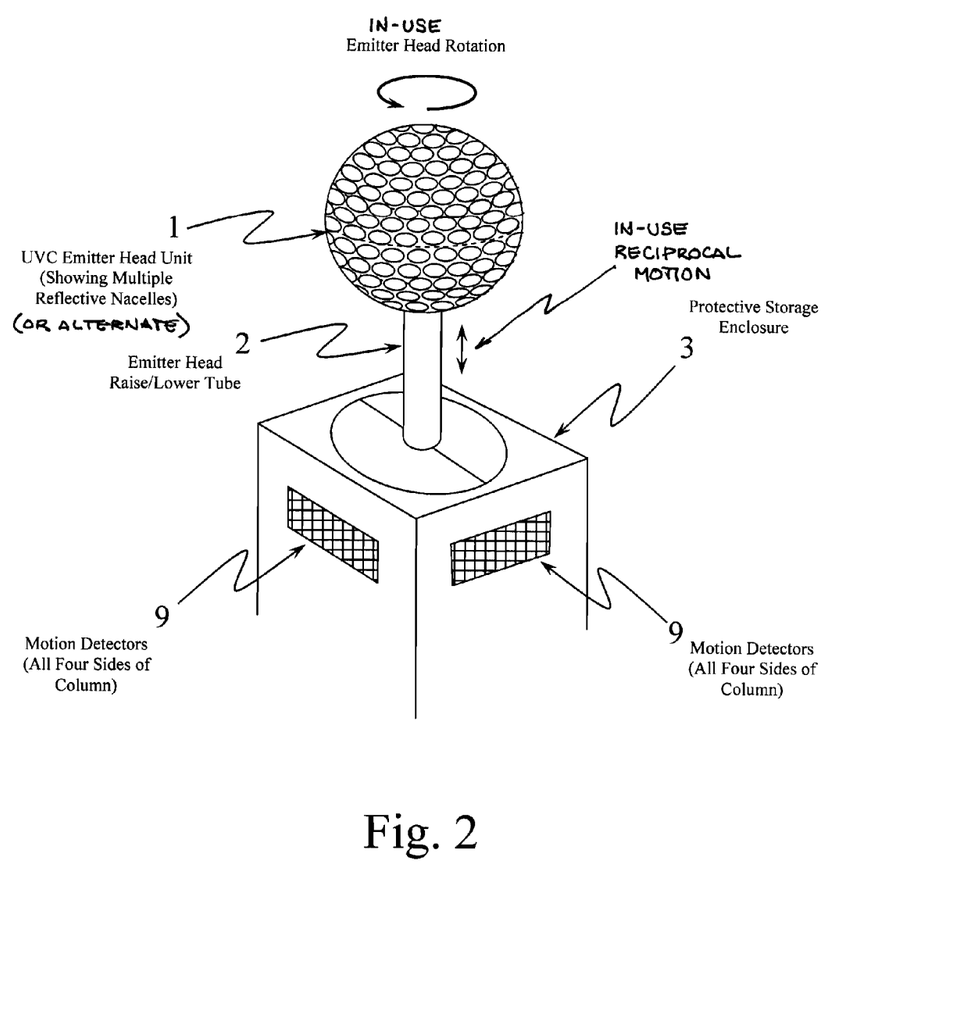
FIG. 2 shows a close-up view of the spherical, rotatable, reciprocal height UV-C emitter head of FIG. 1.

FIGS. 1 & 2 show a general, and close-up view of a free-standing, mobile embodiment of the device, where (1) is a spherical rotatable UV-C emitting structure whose surface consists of densely packed reflective nacels incorporating UV-C energy emitting LEDs or equivalent, concurrent with white light emitter components. Structure (1) is connected to, and supported by, support tube (2), the lower end of which descends into vertical enclosure tower (3), which also functions as a protective enclosure for spherical UV-C emitter (1) when not in use in conjunction with top surface retractable enclosure doors (4). Vertical enclosure tower (3) also contains embedded motion detection sensors (9) on all four sides.

Vertical enclosure tower (3) is, in turn, supported by, and attached to unit base structure (5), which permits device mobility through casters (6). Base structure (5) also contains internal rechargeable battery/AC line driven system power supplies.

Operator mobility control of the described embodiment is provided through handle (7) which also provides enclosure for system control panel (8).

Activation of the described embodiment allows opening of enclosure doors (4) and structure (1) to rise vertically on structure (2) from structure (3). The rise level of structure (2) is determined by the operator to allow optimal height of structure (1) relative to treatment surfaces in its environment. This is accomplished through use of white light system aiming emitters (16) contained in the emitting structure (1).

When optimal system emitter structure (1) aiming is completed and automatic UV-C dosage sensors (13) strategically deployed and activated, the system UV-C start-up is completed, resulting in a (30 second, for example) activation time delay, permitting operator departure from the treatment area. Continuous rotation of UV-C emitting structure (1) begins in conjunction with operator determined steady state or multi-second strobed high intensity overlapping UV-C energy diffusion into the treatment area, enhanced by operator selected reciprocal vertical action of support tube (2).

At automatic or operator pre-selected UV-C dosage sensors (13) cycle completion, or by operator manual control, system shut-down is effected and UV-C emitter structure (1) retracts into protective tower (3). This would also happen automatically should motion detectors (9) determine inadvertent human presence during system activation.

Figure 3A:
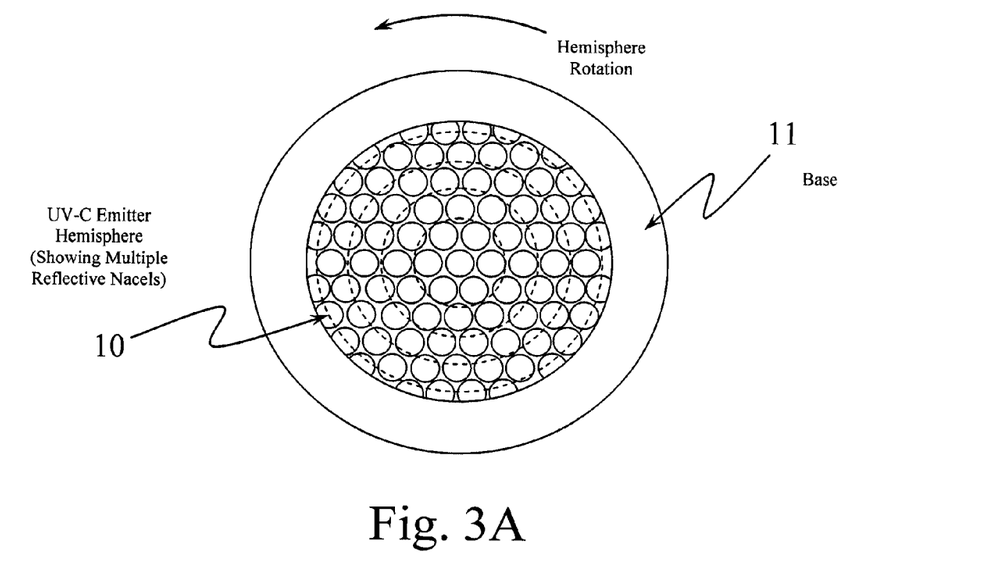
FIGS. 3A & 3B show plan and side views of a hemispherical, rotatable, reciprocal height, permanent ceiling or wall mount embodiment of the UV-C emitter device head. The units may be battery or AC powered and should communicate wirelessly with wall mounted control unit (digital coded).
Figure 3B:
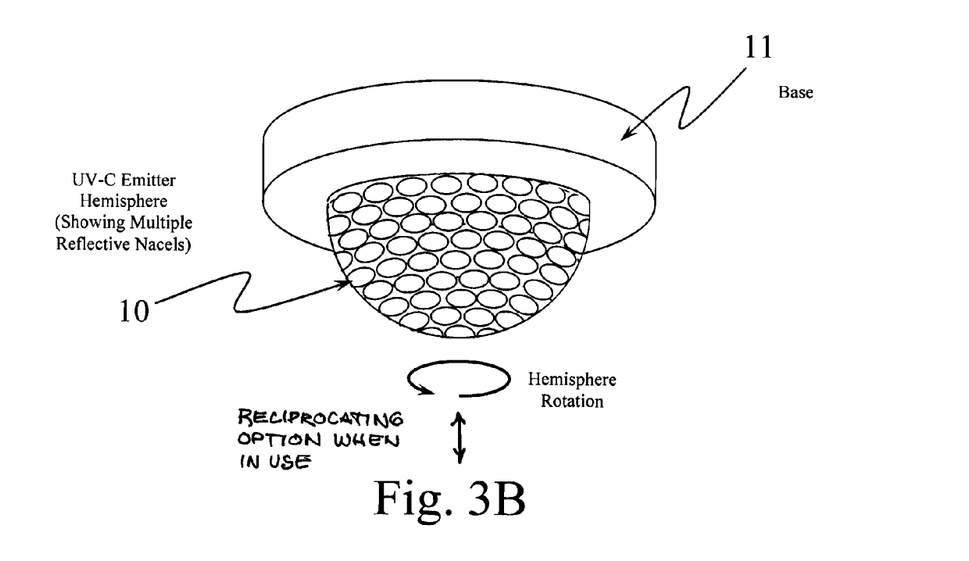
Figure 4:
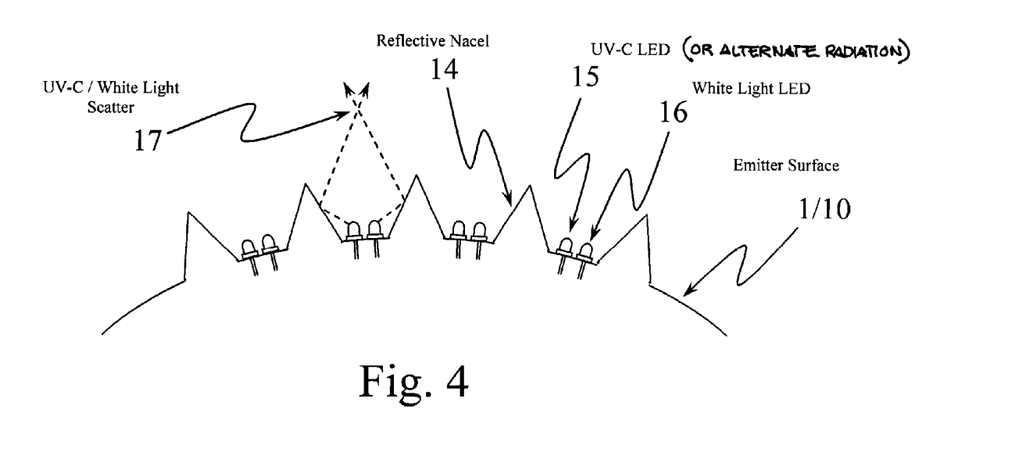
FIG. 4 Shows the cross-section of a number of reflective nacels forming the surface of spherical or hemispherical UV-C device emitter heads. Each nacel incorporates a high intensity UV-C LED (or alternative UV-C energy emission equivalent component) and white light LED mounted within it at an optimal focal point providing effective energy beam or light scatter.
Figure 5:
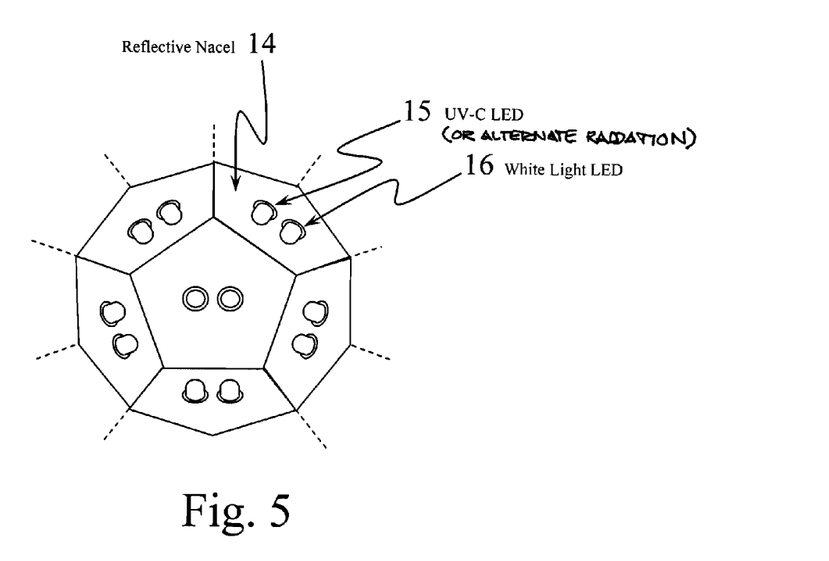
FIG. 5 shows a plan arrangement of hexagonal reflective nacels into a 6 nacel pod. Each pod then interfaces directly with 10 adjacent pods. (Note: alternative geometric nacels are also envisaged as desired within the context of the invention.) Each UV-C LED per nacel is preferably assigned a different wavelength.
Figure 6:
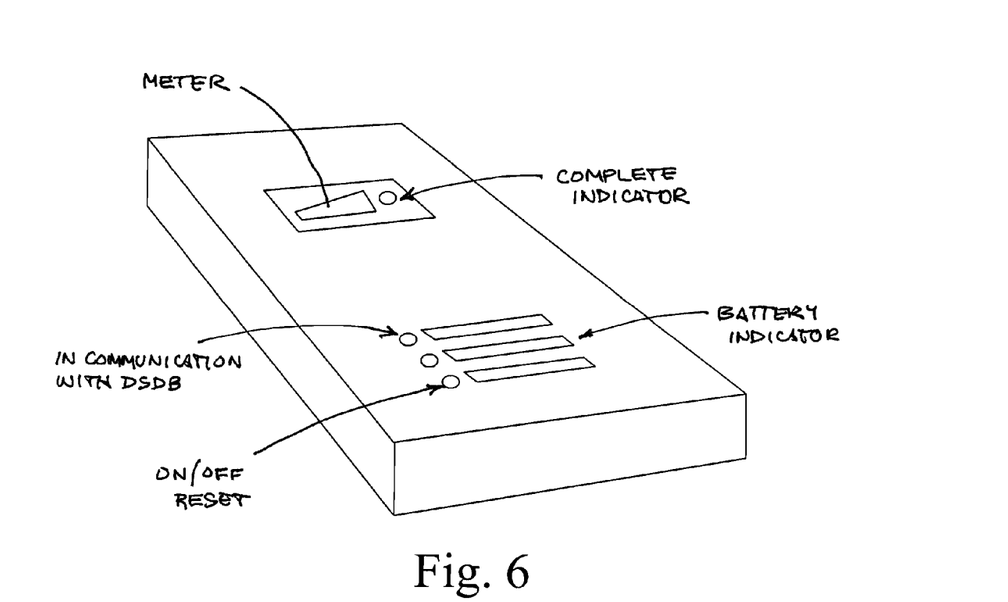
FIG. 6 shows an automatic, self-contained UV-C dosage sensor. Each sensor features an on/off/reset control; a battery condition indicator; a system communication assurance indicator and a display indicating received dosage level of required UV-C energy and dosage completion. The sensor is in wireless communication with the DSDB (the Disinfection Device) through auto detection. The sensor has a self-test/reset function and a specific unique code to the DSDB (digital). When all units are complete, the DSDB shuts off.
Figure 7:
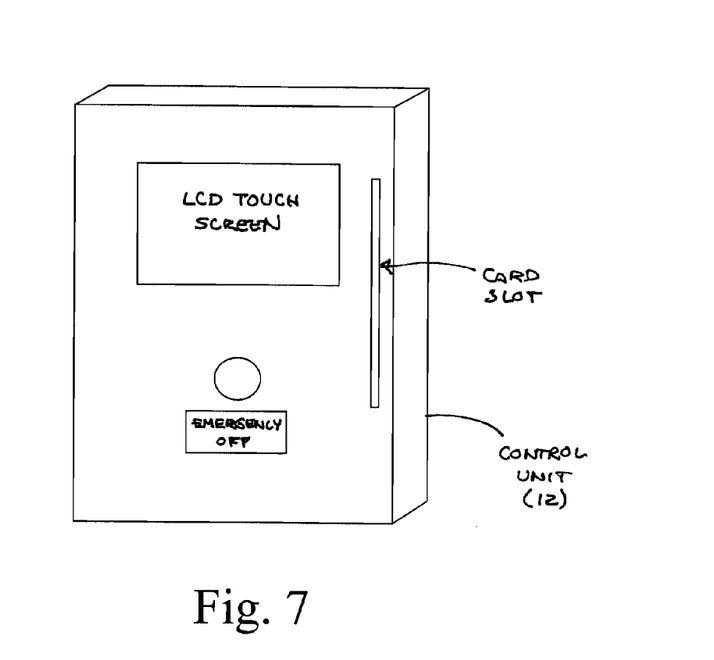
FIG. 7 shows the embodiment of a free-standing UV-C system control unit (intended for wall mounting) and use in conjunction with the hemispherical permanent ceiling or wall-mount embodiment of the device UV-C emitter head unit. The control unit may be battery powered or AC powered. The control unit is in wireless communication with the DSDB unit and the dosage sensors (digital coding).
Figure 8:
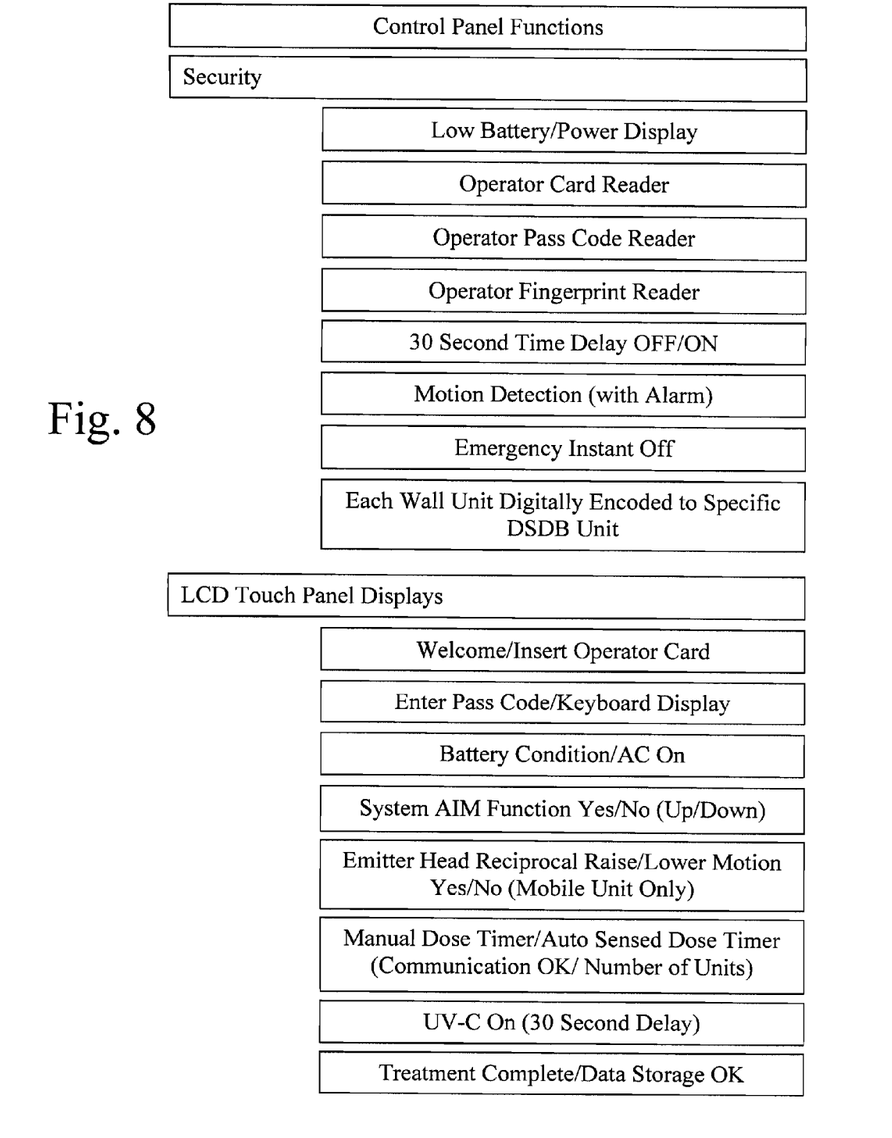
FIG. 8 shows system control unit functions with respect to system security and LCD touch panel displays.

Functionality of the permanent ceiling or wall mount hemispherical UV-C emission embodiment of the device is fundamentally similar with the exclusion of system aiming (completed at installation).

The present invention is therefore directed to:

(A) A spherical, hemispherical, or other geometric shape high energy UV-C emitter head device.

(B) The emitter head device surface consists of densely packed reflective nacels of hexagonal or other geometric cross section.

(C) Each reflective nacel incorporates a high energy UV-C light emitting diode (LED), or other equivalent UV-C energy emitter component.

(D) Each reflective nacel also incorporates a white (or other visible) light LED for emitter head aiming.

(E) Activation power of the high energy UV-C emitter component may be of a steady state nature or strobed multiple times per second.

(F) Each reflective nacel and its immediately surrounding reflective nacels form a pod. Incremental sequencing of differing wavelength high energy UV-C emitter components within a pod produces broad spectrum UV-C energy output from each pod.

(G) Incremental re-sequencing of the pods further enhances the overall diffusion of the broad spectrum high energy UV-C emission from the emitter head assembly.

(H) Rotation of the emitter head assembly further enhances the overall diffusion of the broad spectrum high energy UV-C emission and allows broad treatment area with even UV-C coverage.

(I) Reciprocal vertical motion of the UV-C emitter head assembly in both embodiments of the device further enhances even treatment area coverage by the high energy UV-C emission.

(J) Automatic UV-C dosage sensors monitor effective UV-C irradiation of treatment surfaces during device activation and communicate this data wirelessly to the device for system shut-down once UV-C irradiation is complete.

(K) Multiple system activation and usage security controls are incorporated into the device consisting of (but not limited to):
  (i) Operator system activation microchip embedded card reader and associated passcode keypad assembly.
  (ii) Multi directional treatment area motion sensing during system activation to effect automatic system shut down.
  (iii) Prominently displayed system emergency shut down control.
  (iv) Full digital exclusivity communication encoding between each specific system and its control unit.
  (v) Time delayed system activation from start-up enabling operator treatment area departure.
  (vi) System utilization data storage and retrieval.

(L) System power supplies may be of a rechargeable/battery type or AC line power.

(M) Embodiments of the device may be configured as a free-standing mobile systems or treatment area specific permanent mount systems for ceiling or wall attachment.

I claim:

1. A system for disinfecting a clinical surface, the system comprising:
  broad-spectrum UV-C or alternative ionizing radiation, the radiation produced by a plurality of high-intensity LED's providing emissions at plurality of discrete and differing wavelengths, the LED's oriented to direct the radiation towards the clinical surface;
  a plurality of reflective nacelles, each of the reflective nacelles incorporating one or more of the high-intensity UV-C, or alternative ionizing radiation, LED's, the plurality of reflective nacelles arranged as densely packed groups to form one or more pods, each pod comprising at least two LED's of discrete and differing wavelengths; and
  a rotating, at least partially spherical, support surface on which are positioned the plurality of reflective nacelles, the support surface operating to concurrently reciprocate linearly along its axis of rotation during use for enhanced energy diffusion.

2. The system of claim 1 wherein the plurality of pods are incrementally re-sequenced according to their LED's of discrete and differing wavelengths to produce evenly overlapping output frequency diffusion.

3. The system of claim 1 wherein each of the plurality of reflective nacelles further comprise at least one high-intensity visible light emission LED, permitting initial operator system visible aiming and physical positioning for optimum disinfection performance by the avoidance of radiation shadows.

4. The system of claim 1 further comprising at least one automatic disinfection energy dosage monitor for measuring a quantity of radiation directed towards the subject surfaces or entities.

5. The system of claim 4 wherein the at least one automatic disinfection energy dosage comprise means for wirelessly communicating a signal to direct a system shut-down upon completion of a preset dose of disinfection energy.

6. The system of claim 1 further comprising a multi-directional external motion detection component allowing system shut-down if external motion is detected.

7. The system of claim 1 further comprising a system activation security component providing one or more operator identification protocols.

8. The system of claim 7 further comprising a plurality of individually digitally encoded wireless control components to allow remote control of the system and to prevent control cross-talk.

9. The system of claim 7 further comprising a time-delayed operator activation component, permitting effective treatment area exit time for a system operator.

10. The system of claim 1 wherein the at least partially spherical support surface comprises a hemispherical support surface positioned on a ceiling/wall-mount and the system further comprises a wireless operator control component.

11. The system of claim 1 wherein the at least partially spherical support surface comprises a hemispherical support surface positioned on a ceiling/wall-mount and the system further comprises alternately implemented AC line-power supply and battery power supply, the battery power supply incorporating battery condition indication.

12. The system of claim 1 wherein the at least partially spherical support surface comprises a spherical support surface and the overall system comprises a free-standing system and the system further comprises alternately implemented AC line-power supply and rechargeable battery power supply, the rechargeable battery power supply incorporating battery condition indication.

13. The system of claim 1 wherein the system comprises a mobile free-standing system and means for operator control to provide effective initial physical positioning of the system for optimum disinfection performance.

14. The system of claim 1 further comprising diffusion components, including rotating mirror components and Fresnel lens components.

* * * * *